United States Patent [19]

Spielberg

[11] Patent Number: 5,092,996
[45] Date of Patent: Mar. 3, 1992

[54] BLOOD FILTERING SYSTEM

[75] Inventor: Richard Spielberg, Alameda, Calif.

[73] Assignee: Miles Inc., Elkhart, Ind.

[21] Appl. No.: 656,664

[22] Filed: Feb. 19, 1991

[51] Int. Cl.$^5$ ............... B01D 21/26; B01D 35/02
[52] U.S. Cl. .................. 210/232; 210/257.1;
    210/435; 210/513; 494/20; 494/21; 604/406;
    604/408; 604/410
[58] Field of Search ............ 210/232, 249, 257.1,
    210/435, 513; 494/16, 20, 21; 604/406, 408, 410

[56] References Cited

U.S. PATENT DOCUMENTS

| | | | |
|---|---|---|---|
| 4,157,967 | 6/1979 | Meyst et al. | 210/449 |
| 4,701,267 | 10/1987 | Watanabe et al. | 210/806 |
| 4,880,548 | 11/1989 | Pall et al. | 210/435 |
| 4,923,620 | 5/1990 | Pall | 210/435 |
| 4,925,572 | 5/1990 | Pall | 210/435 |
| 4,985,153 | 1/1991 | Kuroda et al. | 210/789 |

FOREIGN PATENT DOCUMENTS

WO83/01394 4/1983 PCT Int'l Appl. ............... 210/789

Primary Examiner—W. Gary Jones
Attorney, Agent, or Firm—James A. Giblin; Elizabeth F. Enayati

[57] ABSTRACT

A closed blood filter system comprising a filter connected to at least one blood bag, the filter comprising a housing having peripheral support means adapted to hold the filter in place on top of a blood bag centrifuge bucket (cup) and above the blood bags during centrifugation of blood bag contents. In a preferred embodiment the filter is connected between two blood bags by blood bag tubing. A preferred filter housing is generally disk-like and includes an annular projection adapted to fit snugly on the shoulder of a cylindrical centrifuge bucket (cup) while allowing passage of a tubing connecting the top side of the filter with a blood bag held in the centrifuge cup and below the filter.

11 Claims, 4 Drawing Sheets

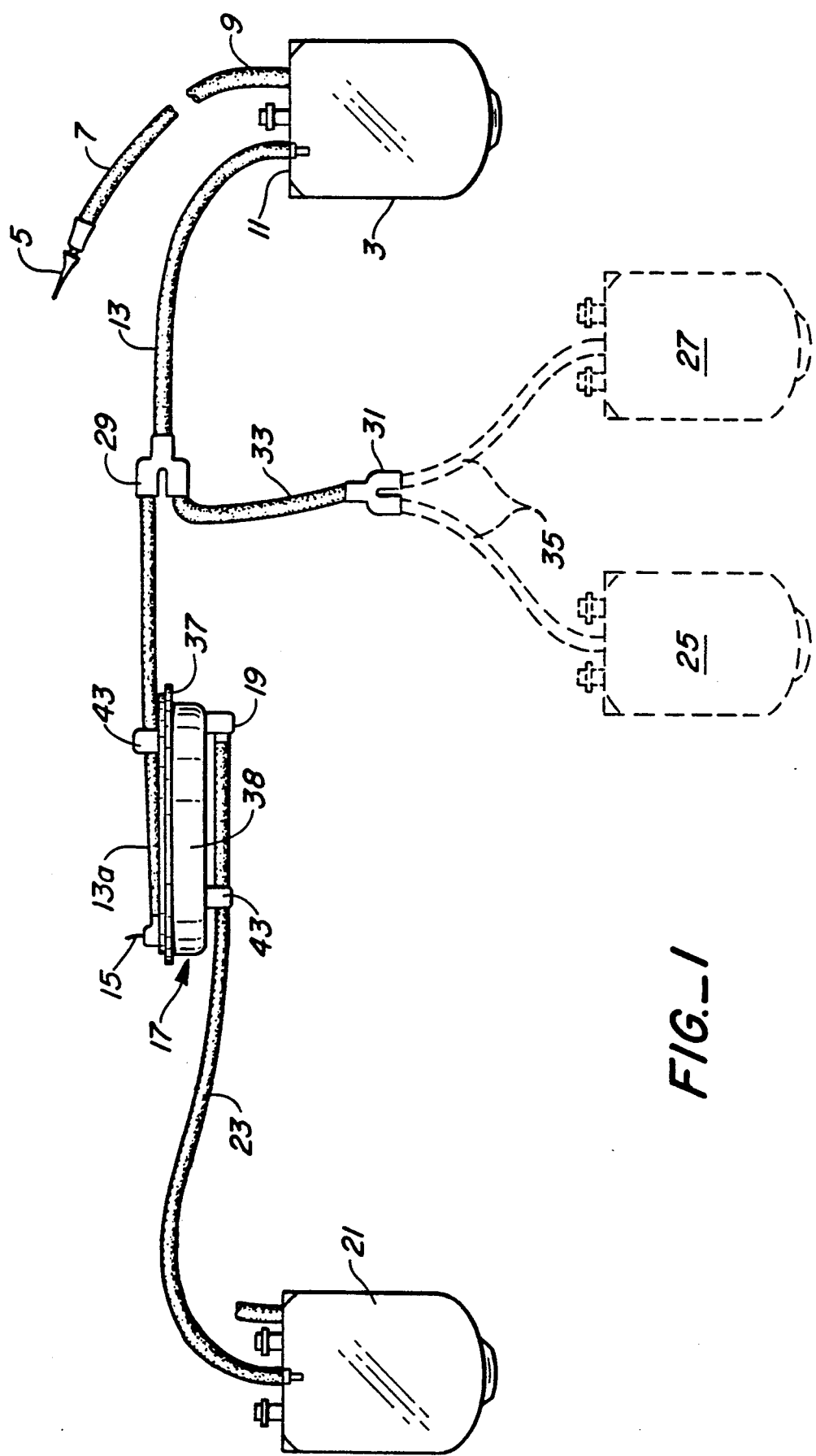
FIG._1

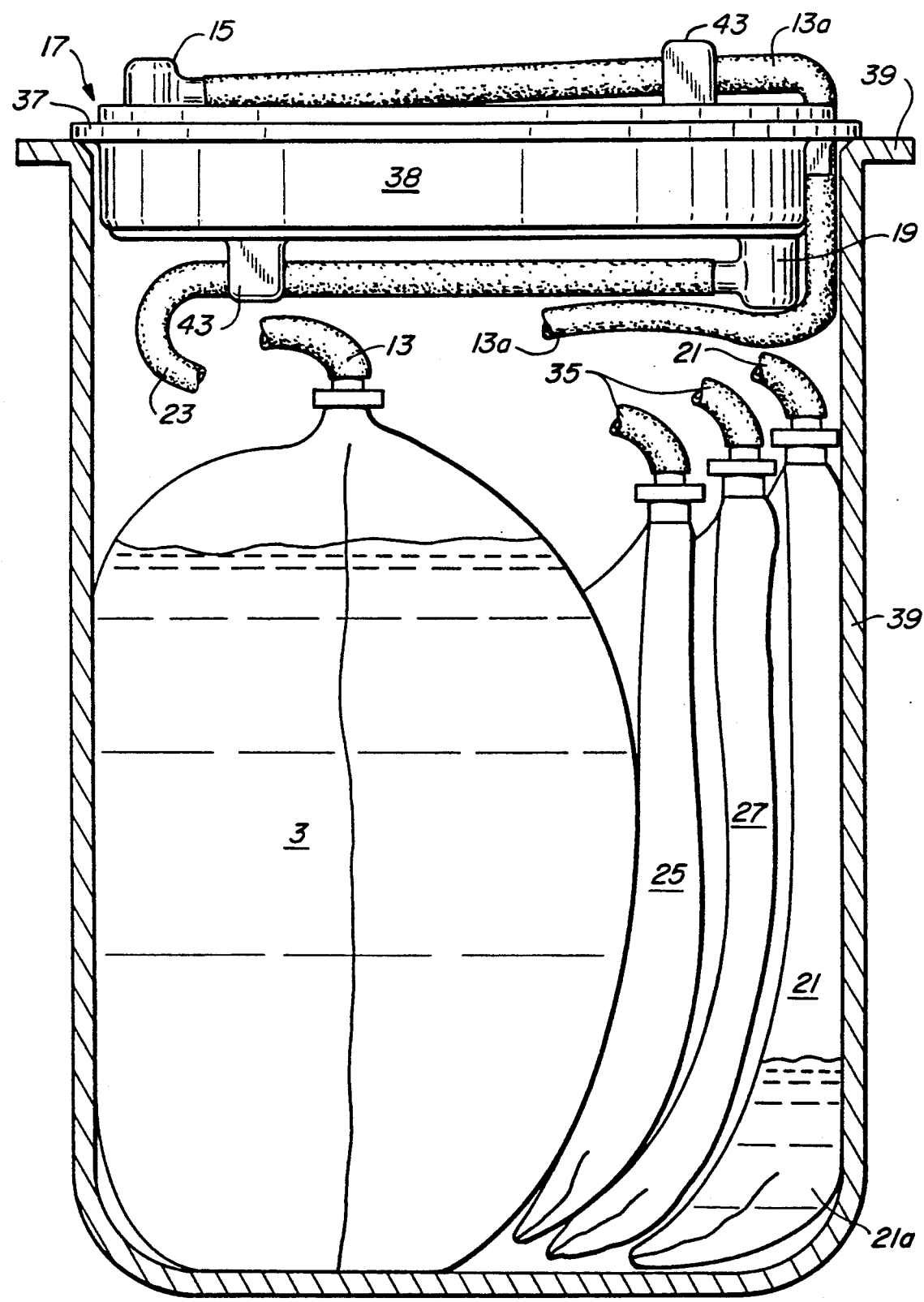
FIG._2

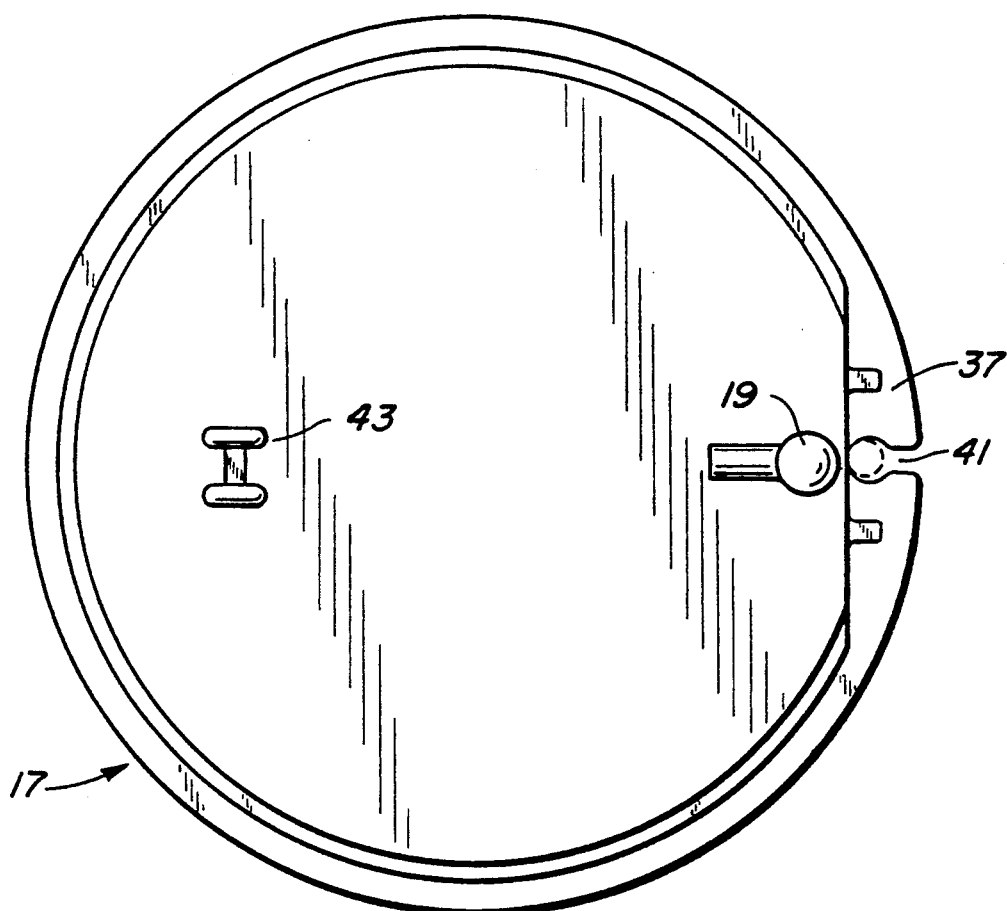
FIG._3
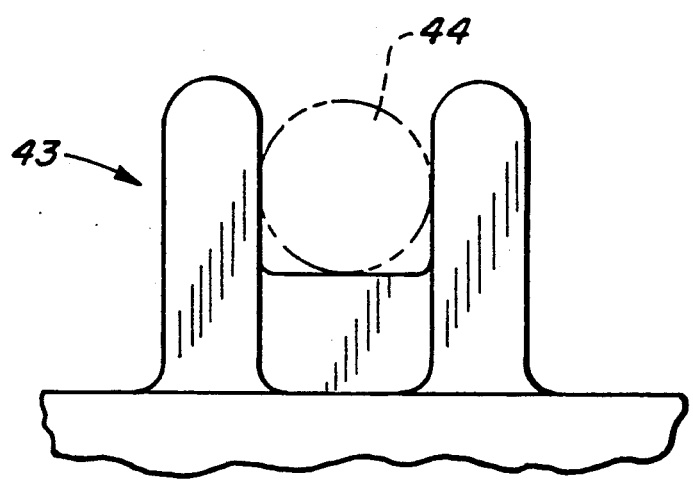
FIG._4

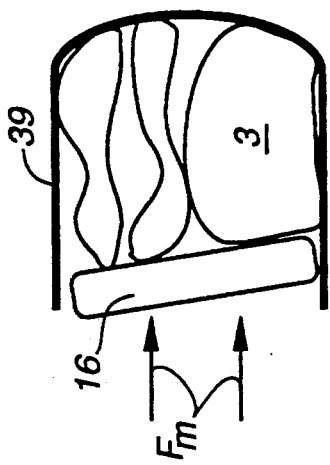
FIG._5C
(PRIOR ART)
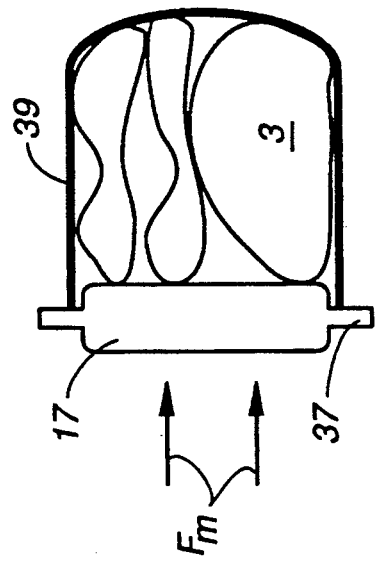
FIG._6C
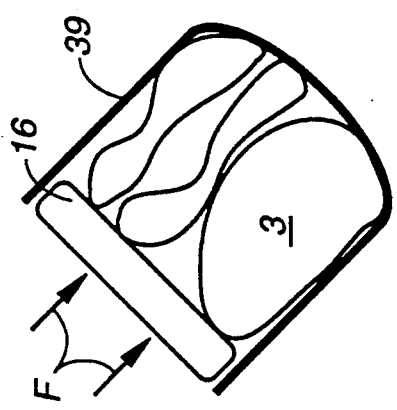
FIG._5B
(PRIOR ART)
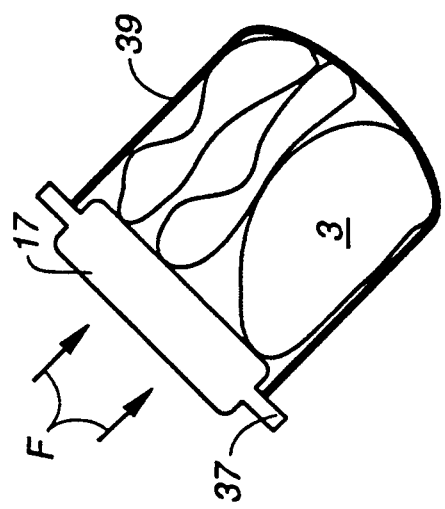
FIG._6B
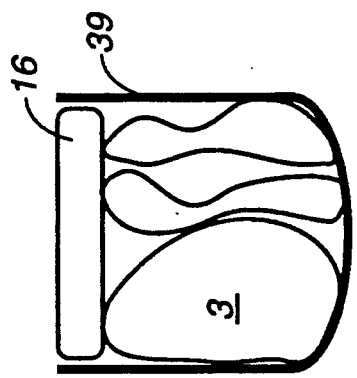
FIG._5A
(PRIOR ART)
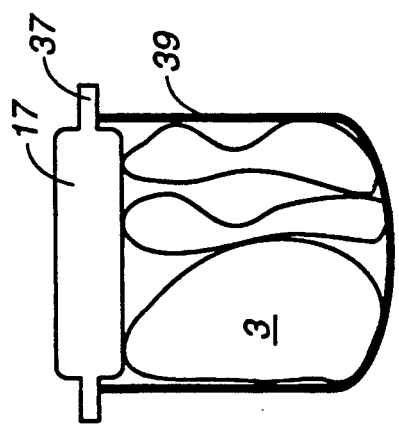
FIG._6A

BLOOD FILTERING SYSTEM

BACKGROUND OF THE INVENTION

1. Field

This disclosure is concerned generally with blood filters and specifically with an improvement in "closed" blood filtration systems.

2. Prior Art

It is well known that whole blood or certain components of whole blood can be filtered to remove undesirable substances such as blood clots, platelets or white blood cells. The present disclosure is especially directed to a blood filter system useful for the removal of white blood cells from red blood cells, platelet concentrates or pools of such concentrates although other blood filtration applications are possible.

In recent years increasing attention has been directed toward the removal of white blood cells (WBCs) from red blood cells and blood components such as platelets. The inclusion of WBCs in blood products is known to cause febrile reactions and alloimmunization when infused in some patients. In addition, it appears that WBC degradation products and/or expressed materials such as enzymes may adversely affect the quality and storage time of blood components. Lastly, WBCs may include viruses which should obviously be excluded from blood products whenever possible.

Diepenhorst et al, Vox. Sang. 23:308–320(1972) disclose one of the early systems for removal of WBCs from blood. In one example blood was passed through a column containing a filter medium in what is considered an "open" system. An open system, as opposed to a "closed" system, is preferably avoided since it assumes the possibility of outside contamination due to the open nature of at least one step. A closed system, on the other hand, is one that assumes no outside contamination, due to the closed nature of the system into which blood is introduced for further processing (i.e., centrifugation, filtration, etc.).

Examples of closed blood bag systems are well known. See, for example, U.S. Pat. No. 4,586,928, to Barnes et al for a definition and examples of a closed blood bag system.

Although the illustrated filtering system of Diepenhorst et al was essentially open and therefore capable of contamination, the authors do describe a system that appears to be a closed multiple blood bag system using a pump to push blood through a filter system. See page 311 of the Diepenhorst et al article.

One of the first illustrations of a truly closed blood filtering system is shown in U.S. Pat. No. 4,596,657 to L. Wisdom. That system shows an in-line WBC filter placed between two blood bags in a "closed" multiple blood bag system. The disclosed filter is cylindrical in shape and connected to the bags via conventional blood tubing. In use, whole blood is collected in a donor bag pre-connected by tubing to the filter at one end of the filter. A second bag is pre-connected by tubing to the opposite end of the filter.

After collection of the whole blood into the donor bag, the blood can be processed (e.g. centrifuged, filtered) under closed system conditions by external manipulation of the contents of individual bags using valves, etc.

Improvements on the above system can be seen in U.S. Pat. No. 4,810,378 to R. Carmen et al showing modifications of the filter fiber and the generally cylindrical filter housing.

Another way to process blood or blood components under "closed" conditions involves using so-called sterile docking (sterile connecting) techniques as shown, for example, in U.S. Pat. No. 4,157,723 to Granzow et al and U.S. Pat. No. 4,507,119 to Spencer. With those techniques, it is possible to attach a filter, under sterile conditions, between two blood bags to accomplish essentially the same results as shown by the L. Wisdom or R. Carmen et al disclosures. A variety of filters can be used and they need not have the generally cylindrical shape disclosed in those patents. For example, the generally disk-shaped filter of U.S. Pat. No. 4,880,548 assigned to Pall Corporation may be used.

Where sterile docking is used, the filter may be attached to a blood bag before or after blood or blood components are added to a bag or the contents have been centrifuged. These are possible advantages but, unfortunately, subject to operator error.

Regardless of whether a pre-connected or a sterile-docked "closed" system is used, however, if centrifugation of the system is contemplated, there have been certain disadvantages that result from centrifuging a closed system consisting of a filter pre-attached to a blood bag containing a fluid. One disadvantage is related to how the pre-connected (or docked) filter should be placed in a centrifuge bucket or cup, especially in the presence of a full donor bag. Conventional blood bag centrifuge buckets have a limited volume which makes it difficult to find room in the bucket for the filter and at least one blood bag filled with whole blood. This becomes even more of a problem when multiple blood bag systems are used, especially if one of the bags also includes an added solution such as a preservative solution to be added to separated components.

Another equally important disadvantage is that, even if it can be placed in the centrifuge bucket, the filter itself may puncture one or more of the bags during the centrifugation process. This can happen because of poor placement of the filter on top of the bags in the bucket or due to edges of the filter housing pressing on the bag(s) during the centrifugation process.

An additional disadvantage is that the filter housing and/or the separation media or seal integrity can be damaged as a result of the centrifugal or differential centrifugal forces.

The above problems have been partially minimized by taking the cylindrical pre-connected filters of the Carmen et al patent and simply placing them on top of the blood bags in the centrifuge bucket. When this is done, however, it is common to have to secure the filter, thus requiring an additional step and part to hold the filter in place above and on the bags in the centrifuge bucket. Even when this is done, there is still a potential for the filter to move and/or to puncture a bag during centrifugation because of its very placement on top of the bags in the centrifuge and the centrifugal forces which push the filter housing into the bags.

Against the above background, I have invented a novel filter system which not only avoids the existing disadvantages but also provides an improved overall filter that permits a relatively quick and efficient filtration of blood. Details of the filter system are described below.

SUMMARY OF THE INVENTION

The closed blood filter system comprises a filter assembly integrally connected to one and preferably to and between at least two blood bags. The filter comprises a housing having peripheral support means adapted to hold the filter in place above and at the top of a blood bag centrifuge bucket during centrifugation of blood bag contents. In use during centrifugation, virtually no added pressure is put on the blood bag(s) held in the bucket and the device itself is exposed to minimal and evenly distributed centrifugal force.

A preferred filter housing is generally disk-like and includes an annular projection adapted or shoulder to fit snugly on the shoulder of the centrifuge bucket or insert cup. To simplify mold design, in a preferred embodiment, the supporting projection has at least one opening for passage of a tubing connecting the top side of the filter with a blood bag held within the bucket. This is especially valuable in systems where the filter is between two bags since it allows the filter inlet and outlet ports to be on opposite sides of the filter.

BRIEF DESCRIPTION OF THE FIGURES

FIG. 1 is a plan view showing an overall filter system having a filter connected between at least two blood bags. The bags are shown in greatly reduced size relative to the filter size.

FIG. 2 shows a cross section of a blood bag centrifugation bucket or insert cup containing multiple blood bags when the filter (not in cross section) is placed on the centrifuge cup.

FIG. 3 is a bottom view of the filter.

FIG. 4 shows a side view of the tubing holder that can be on each side of the filter housing.

FIG. 5A–5C illustrate how pre-connected prior art filters tend to push onto blood bags held within a centrifuge bucket.

FIG. 6A–6C illustrate how the filter system of this disclosure avoids the disadvantages of the prior art.

SPECIFIC EMBODIMENT

FIG. 1 illustrates an example of the closed filter system of this disclosure in its pre-use state, before blood or a blood component is added to one of the bags and before any centrifugation step. All of the blood bags shown in FIG. 1 are considerably reduced in size relative to the size of the filter shown in that Figure.

FIG. 1 shows a donor bag 3 having a pre-connected phlebotomy needle assembly 5 connected via conventional blood tubing 7 to donor bag 3 at port 9 (not shown). Donor bag 3 may have multiple ports, some in connection to other bags, and there must be at least one other port 11 by which blood tubing 13 can be connected to one port 15 of filter 17. Another port 19 on filter 17 preferably connects to a second blood bag 21 via blood tubing 23. Other bags such as 25 and 27 (shown in dotted lines) may be optionally connected to the system as shown at optional Y-connectors 29 and 31 via blood tubings 33 and 35. Peripheral support means 37 can be seen in FIG. 1 and is shown in more detail in FIGS. 2 and 3.

FIG. 2 shows cross sections of a blood bag centrifuge bucket or insert cup 39. In cup 39 are bags 3 and 21 with blood bag 3 shown expanded to indicate it contains blood or a blood component ready for centrifugation. Bag 21 is shown containing a preservative solution 21a and optional bags 25 and 27 are shown empty. Both bags 21 and 3 are connected via tubings to filter housing 17 to form a closed multiple blood bag system. Since the inlet 15 and outlet 19 of filter 17 are on opposite sides of the filter, the peripheral support means 37 must be adapted to allow passage of tubing 13a in FIG. 2 from the top of the filter and into the cup 39 to remain connected to bag 3, now under the filter and in the cup. For clarity, the bulk of the tubings 13, 13a, 23, 33 and 35 are not shown in FIG. 2. However, the relationships of specific tubings to specific bags can be seen by referring back to FIG. 1.

FIG. 3 shows a bottom view of a preferred filter housing showing opening 41 in annular extension 37. Opening 41 allows the passage of tubing from one side of the filter 17 to its opposite side. This unique embodiment greatly simplifies device and mold design. The device can of course be designed with internal communications such that the external connection are on the same side.

In the preferred embodiment, when used with an in line, preconnected, additive solution, two sides of the filter 17 are substantially mirror images of each other. i.e., both sides have tubing inlets 15 or 19 and tubing retention forks 43 for a friction fit of a phantom tubing 44 such as shown in cross section in FIG. 4.

FIGS. 5a, 5b and 5c illustrate how a prior art filter 16 exerts an increasing amount of force (represented by arrows of increasing length F and Fm) on the bags as the centrifuge cup 39 undergoes, from left to right, an increase in rotation speed. In FIGS. 6a, 6b and 6c, however, this undesirable force is avoided from the filter housing of this invention 17 because the peripheral shoulder member 37 restrains downward movement of filter 17 into cup 39.

The external inlet/outlet surfaces of the filter housing are substantially parallel. The filter housing contains filter media such as polyester pads. Other filter media for removing, for example, WBCs are well known. Either side of the filter can be the "inlet" or "outlet" side. A preferred filter housing has a internal volume ranging from about 40 to 15 ml and a thickness of less than about $\frac{1}{2}''$. To fit on a conventional centrifuge bucket, the filter itself (excluding the annular projection) should have an outer diameter of about $3\frac{1}{2}''$, but still fit within the centrifuge cup, preferably just barely. The annular extension should be at least $\frac{1}{8}''$ larger than the inner diameter of any centrifuge bucket used. For most conventional centrifuge buckets, where this invention would be used, the maximum diameter of the housing, including the peripheral shoulder, is about $4\frac{1}{2}''$.

The ratio of the filter fiber housing diameter (excluding the peripheral shoulder) to the filter housing thickness is greater than about 6:1, preferably greater than 8:1. This allows for maximum filtration area/volume and permits the system to be loaded and used without interference with the rotor arms of the centrifuge bucket.

The device is designed to be placed in a conventional blood centrifuge bucket in closed communication with a blood bag, preferably with at least two blood bags of a multiple blood bag system. Typically, one of the bags is filled with whole blood, a mixture of red cells, plasma, platelets and the white blood cells. The other bag may be empty or filled with a given additive solution (i.e., an RBC or platelet preservative solution).

In the preferred embodiment, the filter housing is generally round and disk-like in shape, to maximize filtration surface area, and is sized with a peripheral or annular shoulder having a diameter slightly larger (i.e., at least about ⅛") than the inner diameter of the centrifuge bucket or cup insert (typically about 3¾") so that it fits atop with the main body of the filter just inside the bucket during centrifugation. This placement allows the bag(s) to be spun without pressure on or physical damage to the filled bag from the filter and without disturbance of the blood separation. It also exposes the filter to even and the minimum centrifugal force possible within the bucket during centrifugation.

In red cell leukodepletion, and similarly for platelet rich plasma (PRP) or platelet concentrate leukodepletion, the system of this disclosure provides for filter device placement and usage between a primary (red cell) collection bag and an additive (bidirectional flow) or storage bag. This allows for pre-storage/pre-transfusion leukodepletion in a closed system in the blood bank without any compromise to the microbiological integrity or cellular component dating.

In using the preferred filter shown in FIGS. 1, 2 and 3, coalescing and air elimination is optimal during priming with the filter hung between two bags and turned 90° from the position shown in FIGS. 1 and 2. This positioning utilizes retrograde flow from the bottom inlet. The upward sweep of the inlet flow allows the advancing fluid to fill and displace air. This fluid simultaneously rises and passes through (to the downstream side) and wets/primes the media.

On the downstream, air coming through the media propelled by fluid, easily rises and exits from the top outlet of the filter.

This integrated design provides fast efficient air debubbling and fluid prime. Effective debubbling allows complete usage of the leukocyte media.

In use with a crystalloid prime additive solution, the prime diluent solution also dilutes the concentrated packed cells, reducing their viscosity, resulting in faster flow. During leukodepletion, the (diluted (red)) cell bag is thoroughly mixed and "hung", the flow started in the device with the effluent leukodepleted preparation collected in the (now) empty additive bag. The (bidirectional), housing design allows for the debubbling of any remaining air, rapid exchange of additive for blood in the device and efficient flow during leukodepletion.

The preferred filter incorporates polyester flat sheet filtering (leukodepletion) media in a housing optimized for maximum efficiency in debubbling/priming and filtration in bidirectional flow. The use of polyester flat sheet media is similar to that used in many current filters and these are well known to those skilled in the art of blood filters.

The preferred filter is designed for incorporation into a closed system pre-connected between two (or multiple) bags. In one preferred embodiment, it is designed for bidirectional flow and is positioned between a collection bag and a additive solution bag. In an other embodiment, the filter is connected between collection or pooling bags, and an empty storage bag. In another use the filter is incorporated with a closed blood bag set just prior to use, by sterile docking using an apparatus such as sterile docking devices.

At the end of filtration, when the influent (collection) bag is empty, the upstream/influent areas of the filter will drain as a result of the vacuum formed from the total collapse of the influent bag and tubing. The volume of the filter is designed to be minimal (i.e., less than about 40 ml) so as to minimize the effective hold up volume of the filter after filtration.

In the preferred usage, the filter is provided preincorporated into a sterile blood collection processing set during manufacture. For this usage, the filter system must be designed so that it functions effectively after the routine processing/sterilization steps encountered during blood bag manufacturing, such as irradiation, autoclaving, pasteurization, etc. The filter system must also be designed (shaped) so that during blood component processing it can be not only placed within the top of the centrifuge bucket but also withstand the centrifugal forces used for whole blood separation/fractionation—up to 5000× gravity.

As seen in FIGS. 2 and 3, the device is preferably configured in a round flat shape to allow it's placement as a cap at the top of the centrifuge bucket during blood separation. This placement allows for easy loading of the centrifuge cup (bucket) with minimum usage of cup volume. A holder together with an appropriately sized filter could be designed to accomplish the same goal, but the preferred embodiment simplifies usage.

It should be noted that the relationships among the outer diameter of the support ring, the housing thickness, the position and diameter of the filter housing that actually holds the filter media are somewhat critical because of what can be referred to as a centrifuge's "rotor compartment envelope". This is the volume of space that is available for the filter housing placement within or above the bucket. Once the filter housing is in place above the bucket, it should not interfere with the free swing of the bucket (or be outside the rotor compartment envelope). In swinging bucket rotors, typically used in the blood bank for blood component separation, the swing clearance of the bucket and it's contents as they swing from the vertical to the horizontal position during centrifugation is critical to prevent the device from hitting the rotor body and breaking (the device and bucket contents) and possible damage to the rotor and centrifuge.

The rotor compartment envelope, is unique for each combination of rotor and bucket. It is defined by the angle of the rotor arms, the location of the pivots on the rotor arms (and cup) and the height of the cup. Specifically the following limitations must be considered as critical: the outer edge of the filter housing's peripheral member should not extend past the outside edge of the centrifuge cup, and it must be larger than the inside diameter of the largest bucket. To maximize the space available for the blood bags in the bucket, a portion of the device may extend above the bucket but it must still be within the rotor compartment envelope. In the illustrative example of this disclosure, however, the portion of the housing (not the peripheral shoulder member) holding the filter fiber media is totally within the bucket and below the peripheral shoulder member. The diameter of the filter body (housing the media) should be as large as possible, but smaller than the smallest bucket inside diameter. The device thickness and thus the thickness of the media pad, should be kept as small as possible to provide fast flow, but enough media must be present to provide the required cell depletion.

Taking into consideration the above limitations, a filter housing was made within the following dimensions.

Peripheral support member
Outside diameter: 3 15/16"–4⅛"
Thickness: 1/16"–¼"
  Main filter body (filter media holder)
Outside diameter 2"–3 15/16"

Thickness: ¼"-¾"

In general, the ratio of filter housing thickness to housing diameter, including the peripheral shoulder or support member, should be at least about 6:1, preferably about 8:1. Although the percentage of filter body (housing holding the filter media) inside the bucket may range from 0-100% (it is 100% in FIG. 2), it should be understood that if more volume is needed for blood bags within the bucket then much, if not all of this volume (see item 38 in FIG. 2), may be located above the top of the bucket. For example, the filter of FIG. 2 could be turned up-side-down so that as much as 100% of that volume (see item 38 of FIG. 2) is outside of the bucket volume and above the peripheral shoulder member, thus allowing more volume in the bucket for blood bags.

The only constraint on such a reversal is that the volume of the housing extending above the top of the bucket (item 38 of FIG. 2) must fall within the rotor compartment envelope. However, it can be appreciated that by having item 38 extend at least slightly into the bucket, the filter assembly of FIG. 2 is less likely to slip off of the bucket, especially when the bucket is spinning.

Given the above disclosure, it is thought that numerous variations will occur to those skilled in the art. Accordingly, it is intended that the above examples should be considered illustrative only and that the invention disclosed should be limited only by the following claims.

I claim:

1. A closed blood filtering system comprising:
   a generally disk-shaped filter housing for holding filter media, and
   a peripheral shoulder member that laterally extends beyond said filter housing by an amount sufficient to fit on the top of a centrifuge bucket and to prevent said filter housing from entering said bucket during centrifugation, said filter being connected by tubing to at least one blood bag.

2. The system of claim 1 wherein the housing is connected by tubing to at least two blood bags.

3. The system of claim 2 wherein the tubings connecting each of the two blood bags are connected to opposite sides of the filter and the shoulder member includes means for passage of at least one tubing from one side of the filter housing to the opposite side.

4. The system of claim 1 wherein the ratio of housing diameter, excluding the peripheral shoulder member, to filter housing thickness is at least about 6:1.

5. The system of claim 4 wherein the ratio of housing diameter, excluding the peripheral shoulder member, to filter housing thickness is at least 8:1.

6. The system of claim 1 wherein the diameter of that portion of the housing holding the filter media, excluding the peripheral shoulder member, is in the range of 50 to 95% of the largest diameter of the filter housing, including the peripheral shoulder member.

7. The system of claim 6 wherein the diameter of the housing holding the filter media is at least 85% of the largest diameter of the filter housing, including the peripheral shoulder member.

8. The system of claim 1 wherein that portion of the filter housing holding the filter media extending below the peripheral shoulder member ranges from 0 to 100% by volume.

9. The system of claim 8 wherein that portion of the filter housing holding the filter media extending below the peripheral shoulder member is at least 90%.

10. The system of claim 9 wherein the entire portion of the housing holding the filter media is adapted to extend entirely below the peripheral shoulder member.

11. The system of claim 1 wherein at least a portion of the filter housing holding the filter media extends above the peripheral shoulder member.

* * * * *